(12) United States Patent
Davey

(10) Patent No.: US 6,358,230 B1
(45) Date of Patent: Mar. 19, 2002

(54) PERCUTANEOUS CATHETER WITH SLIP HUB

(75) Inventor: Christopher T. Davey, Boston, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/163,153

(22) Filed: Sep. 29, 1998

Related U.S. Application Data

(60) Provisional application No. 60/060,624, filed on Oct. 1, 1997.

(51) Int. Cl.$^7$ .................................................. A61M 5/32
(52) U.S. Cl. ..................................................... 604/177
(58) Field of Search ............... 604/523, 165.01–165.04, 604/177

(56) References Cited

U.S. PATENT DOCUMENTS

| | | | |
|---|---|---|---|
| 3,589,361 A | * 6/1971 | Loper | 604/523 |
| 3,782,383 A | * 1/1974 | Thompson et al. | 604/177 |
| 5,088,982 A | * 2/1992 | Ryan | 604/523 |
| 5,195,985 A | * 3/1993 | Hall | 604/195 |
| 5,322,514 A | * 6/1994 | Steube et al. | 604/177 |
| 5,330,449 A | * 7/1994 | Prichard et al. | 604/523 |
| 5,596,988 A | * 1/1997 | Markle et al. | 128/635 |
| 5,618,587 A | * 4/1997 | Markle et al. | 128/635 |
| 5,685,858 A | * 11/1997 | Kawand | 604/171 |

\* cited by examiner

*Primary Examiner*—Anhtuan T. Nguyen
*Assistant Examiner*—Michael M Thompson
(74) *Attorney, Agent, or Firm*—Testa, Hurwitz & Thibeault, LLP

(57) ABSTRACT

A "slip" hub design is used with catheters to reduce flexure motion at the hub to catheter shaft connection. The design includes a hub having a section of reduced diameter and having a longitudinal axis extending along the length of the hub. The reduced diameter section has a first length. The design also includes a suture wing component having a first portion with a lumen. Wings extend from the first portion, and in use are sutured to the skin of a patient, or to an anchoring device that is secured to the skin of a patient. The lumen has a second length that is less than the first length. The reduced diameter section of the hub is disposed within the lumen such that the axis extends through the lumen and such that the hub and the suture wing component are movable relative to each other both axially along the axis and rotationally about the axis.

5 Claims, 4 Drawing Sheets

PERCUTANEOUS CATHETER WITH SLIP HUB

CROSS-REFERENCE TO RELATED APPLICATION

This incorporates by reference and claims priority to and the benefit of U.S. povisional patent application Ser. No. 60/060,624, filed Oct. 1, 1997.

TECHNICAL FIELD

The invention relates generally to catheters for use in a body. More particularly, the invention relates to a "slip" hub design for use in a percutaneous catheter in a body.

BACKGROUND INFORMATION

Long term indwelling percutaneous catheters, such as peripherally-inserted central catheters (PICCs), central lines, and hemodialysis catheters, are widely used for a variety of medical applications (e.g., administration of drugs, drawing blood, etc.). These catheters have a rigid hub that is typically sutured to the skin to prevent the catheter shaft from being inadvertently pulled out. More specifically, suture wings are rigidly connected to the hub and sutured to the skin. The catheter shaft extends from the sutured hub, through the skin and underlying tissue, into the vascular system and ends at the junction of the superior vena cava and the right atrial (i.e., the SVC/RA junction). The catheter is maintained in this position over several weeks or months.

During this period of time, the patient is typically fully ambulatory. Since the hub is rigidly fixed to the patient (i.e., via the suture wings) and the catheter shaft is relatively fixed within the percutaneous entry site, all relative motion between these two locations imparts flexural stress on the hub to catheter shaft connection. As the patient moves about over the period of time (e.g., several weeks or months) that the catheter is in use, the rigid connection between the hub and patient focuses all the resulting flexural motion on the hub to catheter shaft connection. Over time, this stress often leads to mechanical failure at the hub to catheter shaft junction, which requires the removal and replacement of the failed catheter. For example, an article entitled "PICC Lines: Choosing Devices, Placement and Management" by Dr. Alan Matsumoto reports a 9.7% mechanical failure rate of the device at the hub to catheter shaft junction.

SUMMARY OF THE INVENTION

It is a principle object of the invention to reduce the mechanical failure rate of catheters, such as long term indwelling percutaneous catheters. It is another object of the invention to provide a long term indwelling percutaneous catheter that offers a flexible connection between the hub and suture wings such that a percentage of the flexural motion is absorbed at that area, thereby reducing the stress on the hub to catheter shaft connection and extending the service life of the catheter.

These and other objects are met by a "slip" hub design according to the invention. With catheters employing this type of new hub design, the rate of mechanical failure of the catheters (such as long term indwelling percutaneous catheters) is reduced, and the catheters can be maintained in position in patients' bodies for an extended period of time, such as several weeks, several months, or longer.

The invention features a catheter (such as a long term indwelling percutaneous catheter) that includes an elongated catheter shaft, a hub, and a suture wing component. The elongated shaft has a proximal end and a distal end, where the distal end is for insertion into a body. The distal end of the catheter shaft enters the body at an entry site. The entry site can be a puncture of the skin of the body that leads to a vein within the body into which the catheter shaft is inserted, for example. The hub is located at or near the entry site of the body. A suture wing component is placed over (and surrounds) a portion of the hub. The suture wing component is secured to the skin of the body, or to an anchoring device that is itself secured to the skin of the body, adjacent the entry site. The catheter shaft extends through the hub, through the skin and underlying tissue, and into the vascular system (e.g., into a vein) of the patient's body such that the distal tip of the catheter shaft can be located at a desired point in the body, such as at the SVC/RA junction. The catheter can be maintained in this position within the body for an extended period of time, such as for several weeks, several months, or longer. The hub includes a section of reduced diameter, which is engaged and surrounded by a portion of the suture wing component. The reduced diameter section allows the hub to move substantially unrestricted translationally (i.e., axially, back and forth along a longitudinal axis of the hub and catheter) and rotationally relative to the suture wing component. In one embodiment, the suture wing component includes a rounded edge adjacent the hub. The rounded edge of the suture wing component allows an additional degree of freedom of relative movement between the hub and the suture wing component, such that the hub can "rock" within the suture wing component.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

In one aspect, the invention relates to a catheter comprising an elongated member, such as a catheter shaft, a hub, and suture wing component. The elongated member includes a proximal end and a distal end, the-distal end being insertable into a body at an entry site of the body. The hub is connected to the proximal end of the elongated member, and it is disposed at the entry site. The hub includes a section of reduced diameter, and a longitudinal axis extends along the length of the hub. The suture wing component is for securing to the body adjacent the entry site. Alternatively, the suture wing component can be secured or attached to an anchoring device that is itself secured to the skin of the body adjacent the entry site. The suture wing component surrounds a portion of the reduced diameter section of the hub at the entry site, thereby enabling the hub to move both along and about the axis relative to the suture wing component.

In another aspect, the invention features a system comprising a hub and a suture wing component. The hub is for use with a catheter. The hub includes a section of reduced diameter and has a longitudinal axis extending along its length. The reduced diameter section has a first length. The suture wing component has a first portion with a lumen and wings extending from that first portion. The lumen has a second length that is less than the first length. The reduced diameter section of the hub is disposed within the lumen such that the axis extends through the lumen and such that the hub and the suture wing component are movable relative to each other both axially along the axis and rotationally about the axis.

In some embodiments of the invention, the suture wing component comprises a rounded edge that allows the hub to have additional freedom of movement relative to the suture wing component, such that the hub can "rock" within the suture wing component.

In general, according to the invention, a "slip" hub design is provided for a flexible catheter 2, such as a long term indwelling catheter, including a percutaneous central venous catheter. The catheter 2 is shown generally in FIG. 4 outside of the body. A "slip" hub of the invention has a section of reduced diameter, which allows the hub to move in a substantially unrestricted manner relative to suture wings, which in use are sutured to the patient's skin. A "slip" hub design of the invention better distributes flexural stresses among the patient's skin, the catheter shaft, and the catheter hub. The "slip" hub reduces flexure motion at the hub to catheter shaft connection and thus reduces the frequency of field failures resulting from the catheter breaking from the hub.

Figure 1:
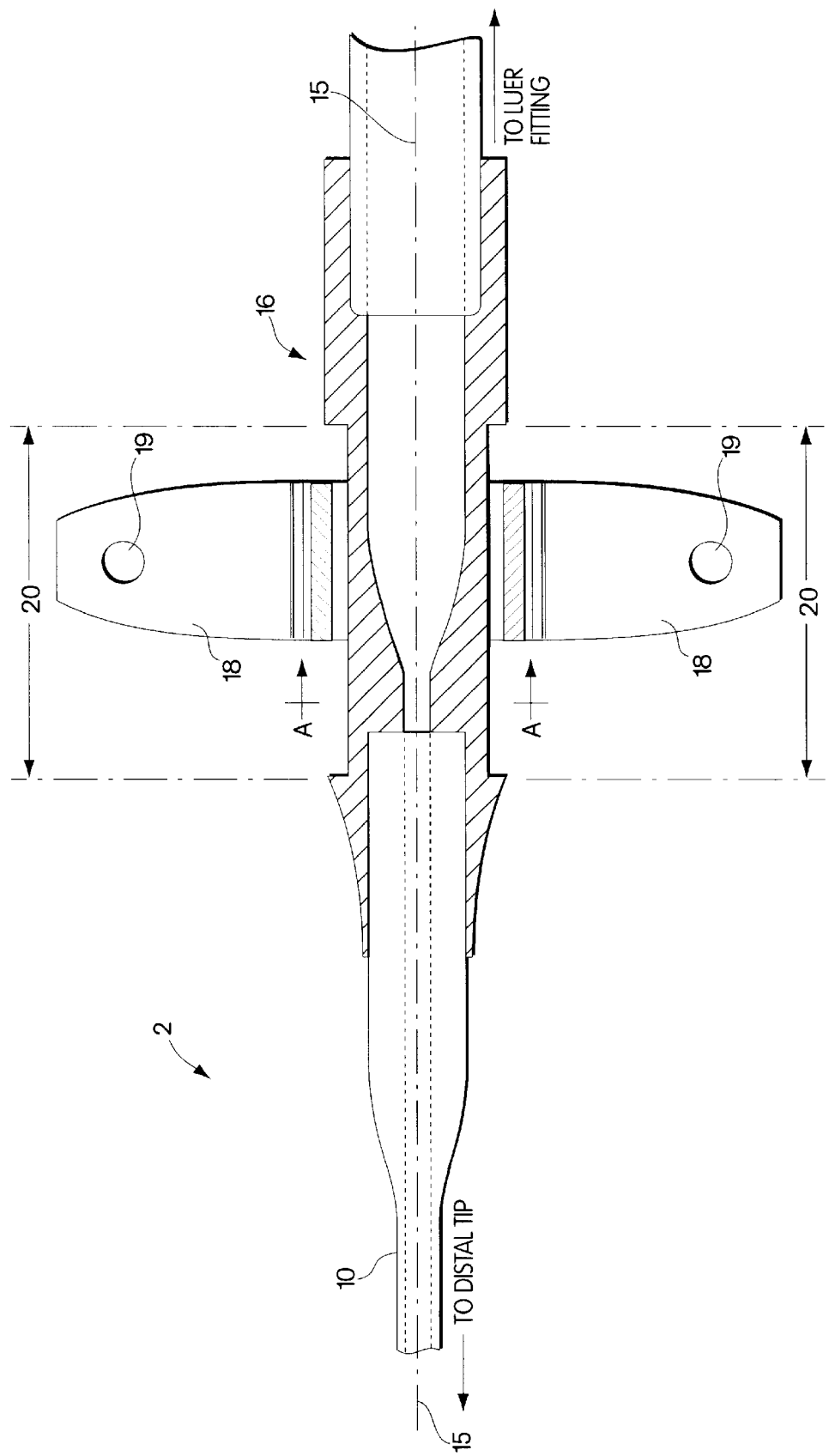
FIG. 1 is a cross-sectional view taken along section B—B of FIG. 2 of a long term indwelling percutaneous catheter incorporating the principles of the invention.
Figure 2:
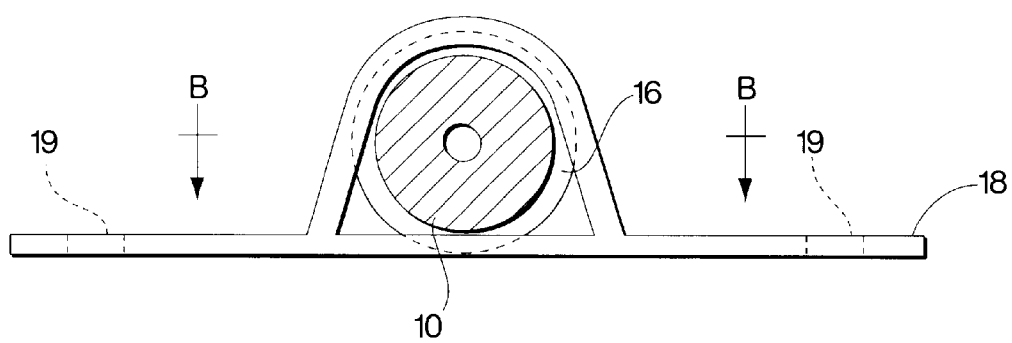
FIG. 2 is a cross-sectional view taken along section A—A of the catheter of FIG. 1.
Figure 4:
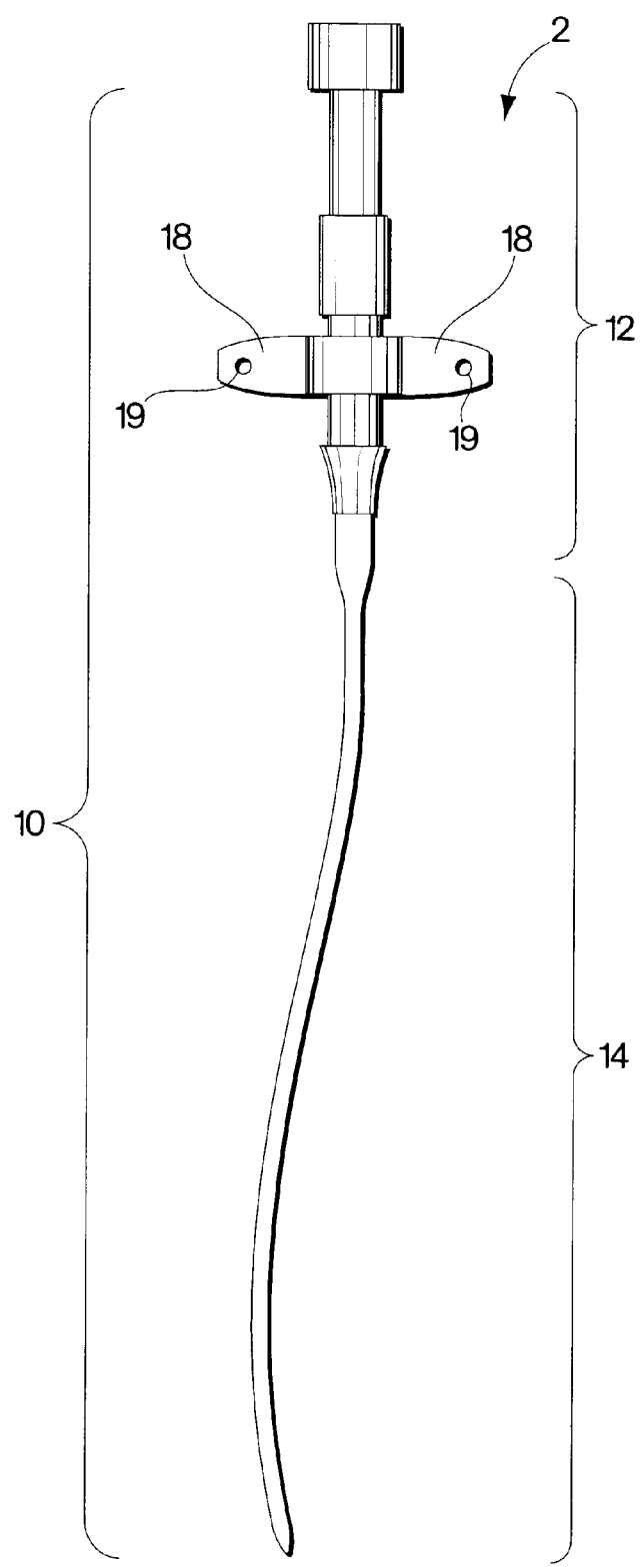
FIG. 4 shows a catheter generally, such as an indwelling percutaneous catheter.

FIG. 1 is a cross-sectional view taken along section B—B of FIG. 2 of a long term indwelling percutaneous catheter 2 that includes a "slip" hub design of the invention. As shown in FIG. 4, the catheter shaft 10 has a proximal end 12, and a distal end 14, which is for placement within the body of the patient. As shown in FIGS. 1 and 4, the hub 16 is located at or near an entry site of the body, and a suture wing component 18 is located over or about the hub 16. A portion of the suture wing component 18 surrounds a portion of the hub 16 that has a reduced diameter. That is, the suture wing component 18 has a first portion with a lumen, and the reduced diameter section 20 of the hub 16 is disposed within this lumen such that the lumen and the hub are coaxial with respect to the longitudinal axis 15. The suture wing component 18 fits in this reduced diameter section of the hub 16, but it fits in a way that it has some "play" to allow relative movement, both axial and rotational, between the hub 16 and the suture wing component 18. The hub 16 can be an integral part of the catheter 2, the catheter 2 and the hub 16 can be disconnectable from each other, or the hub 16 can be assembled to the catheter 2 in such a way that they are practically unremovable from each other in the field. Different assembly, connection/disconnection, and manufacturing schemes generally are known, and the actual assembly details are generally less central to the invention than the ability provided by the invention to have both longitudinal and axial relative motion between the hub 16 and the suture wing component 18.

When the suture wing component 18 is not attached (e.g., sutured) to the skin of the patient, or not attached to an anchoring device that is itself secured to the skin of the patient, the suture wing component 18 can substantially freely spin or rotate within the reduced diameter section 20 of the hub 16 about the longitudinal axis 15, and it also can substantially freely move back and forth (i.e., axially with respect to the longitudinal axis 15) within the travel range of the reduced diameter section 20 of the hub 16. In one embodiment, the travel range is 5 millimeters or about 5 millimeters. In one embodiment, the diameter of the reduced diameter section 20 of the hub 16 is between about 1 millimeter to about 3 millimeters, and preferably it is 2 millimeters or about 2 millimeters. The suture wing component 18 has at least one pre-formed hole or puncture 19 near the end of each wing to allow attaclunent (e.g., suturing) to the skin of the patient to hold the suture wing component 18 secure when the catheter 2 is in use and in place within the body. When secured to the skin, or to an anchoring device that is secured to the skin, the suture wing component 18 stays substantially stationary, and movement of the patient and/or the catheter 2 typically will result in the hub 16 rotating within the suture wing component 18 about the axis 15 and moving axially back and forth with respect to the axis 15 over all or a portion of the travel range of the reduced diameter section 20 of the hub 16. Another view of the suture wing component 18 is shown in FIG. 2.

In use, the catheter shaft 10, which extends into and typically through the hub 16, enters the body via an entry site of a body, such as, for example, a puncture of the skin of the body. One example of a catheter of the invention would be a percutaneous central venous catheter having the "slip" hub design. The distal portion of the shaft of percutaneous central venous catheter can extend through the skin and underlying tissue, into the vascular system (e.g., a vein), and end at the SVC/RA junction. Because of the "slip" hub design, the catheter can be maintained in this position for a period of several weeks, several months, or longer, without the mechanical failure associated with conventional indwelling catheters.

The reduced diameter section 20 of the hub 16 thus allows the hub 16 to move in a substantially unrestricted manner back and forth (i.e., longitudinally or axially along the axis 15) and rotationally (i.e., about the axis 15) relative to the suture wing component 18.

Figure 3:
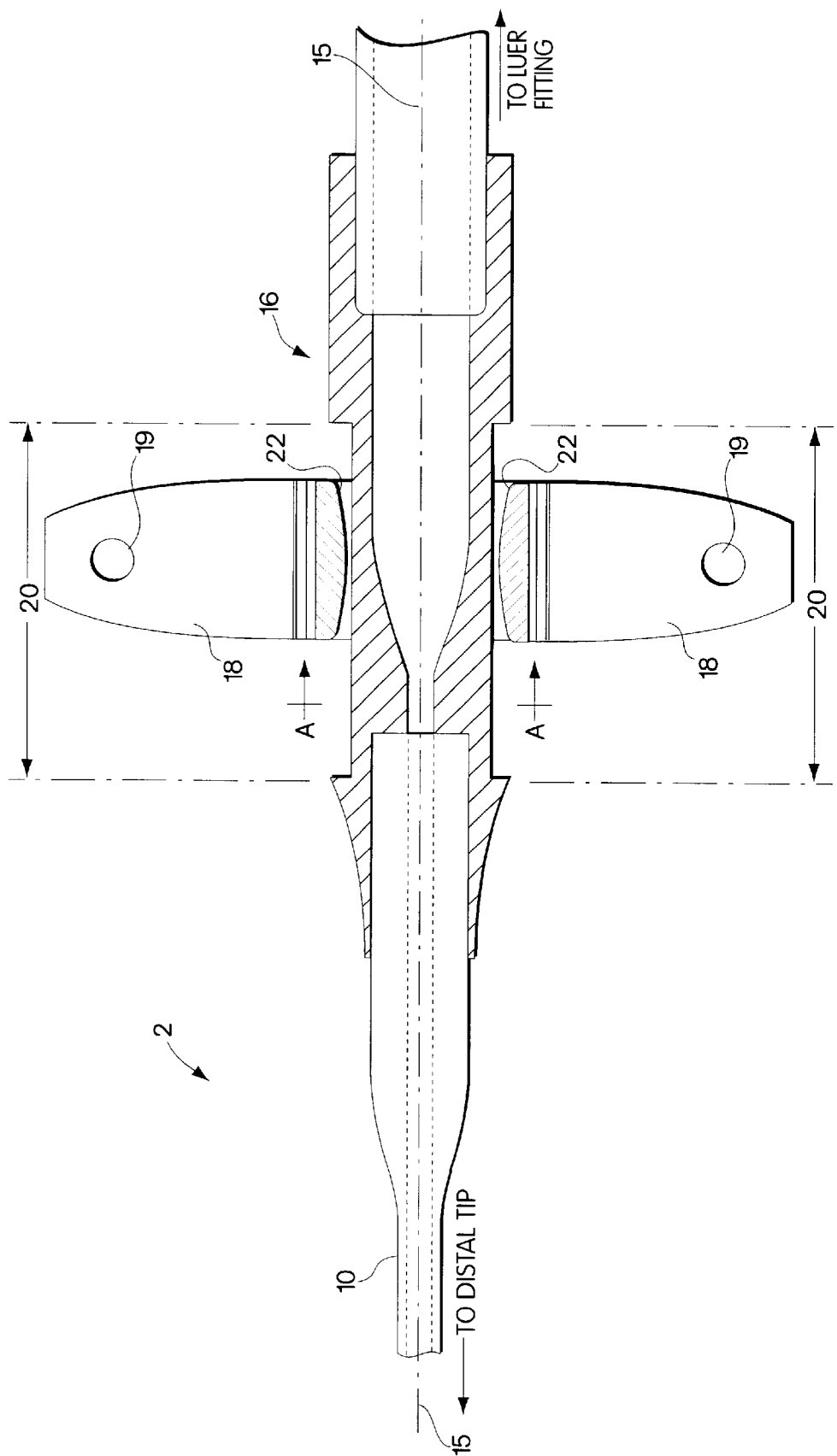
FIG. 3 is a partial cross-sectional view of an alternative embodiment suture wing component in a long term indwelling percutaneous catheter.

FIG. 3 shows an embodiment of the invention in which the suture wing component 18 has a rounded edge 22 adjacent the reduced diameter section 20 of the hub 16. The rounded edge 22 allows the hub 16 to "rock" within the suture wing component 18. Like the other hub design (FIGS. 1 and 2), this alternative design also reduces the flexure motion at the hub to catheter shaft connection, and acts to extend the service life of the catheter.

The invention allows for greater relative motion between the hub 16 and the suture wing component 18 than possible with conventional catheters. With the invention, flexural forces can be distributed over two junctions (suture wing component to hub and, catheter shaft to hub), rather than just one (catheter shaft to hub), thus extending the life of the catheter. In one embodiment, the amount of relative motion permitted between the hub 16 and suture wing component 18 may be limited to much less than one square centimeter of the patient's skin surface, which would have little or no impact on the catheter's distal tip location within, for example, the SVC/RA junction. This motion, however, greatly reduces the flexing and stress associated with conventional catheters.

Variations, modifications, and other implementations of what is described herein will occur to those of ordinary skill in the art without departing from the spirit and the scope of the invention as claimed. Accordingly, the invention is to be defied not by the preceding illustrative description but instead by the spirit and scope of the following claims.

What is claimed is:

1. A system, comprising:

a monolithic hub for use with a catheter, the hub including a proximal portion and a distal portion, and a intermediate section of reduced external diameter between the distal portion and the proximal portion and having a first length; and a suture wing component having a first portion with a lumen and wings extending from the first portion, the first portion having a second length less than the first length, whereby the first portion lumen permanently surrounds the intermediate reduced external diameter section of the hub such that the hub and the suture wing component are freely movable relative to each other both axially and rotationally.

2. The system of claim 1, wherein the suture wing component comprises a rounded edge thereby allowing the hub to have additional freedom of movement relative to the suture wing component.

3. A catheter, comprising:

an elongated member including a proximal end and a distal end, the distal end being insertable into an entry site of a body;

a monolithic hub including a proximal portion and a distal portion connected to the proximal end of the elongated member, the hub including a longitudinal axis and a section of reduced external diameter between the distal portion and the proximal portion; and a suture wing component securable to an external portion of the body, the suture wing component permanently surrounding a portion of the intermediate reduced external diameter section of the hub at the entry site thereby enabling the hub to freely move both along and about the axis relative to the secured suture wing component.

4. The catheter of claim 3 wherein the suture wing component comprises a rounded edge thereby allowing the hub to have additional freedom of movement relative to the suture wing component.

5. The catheter of claim 3, wherein said suture wing component is configured to be attachable to an anchoring device secured to skin of said body.

\* \* \* \* \*

UNITED STATES PATENT AND TRADEMARK OFFICE
CERTIFICATE OF CORRECTION

PATENT NO. : 6,358,230 B1
DATED : March 19, 2002
INVENTOR(S) : Davey

It is certified that error appears in the above-identified patent and that said Letters Patent is hereby corrected as shown below:

<u>Title page,</u>
Item [56], References Cited, U.S. PATENT DOCUMENTS, add the following United States Patents,

| | | | |
|---|---|---|---|
| -- 4,114,618 | 9/1978 | Vargas ............................ | 604/165.01 |
| 4,392,856 | 7/1983 | Lichenstein ....................... | 604/177 |
| 4,643,711 | 2/1987 | Bates .............................. | 604/6.16 |
| 4,676,782 | 6/1987 | Yamamoto et al. ................... | 604/175 |
| 4,772,268 | 9/1988 | Bates .............................. | 604/174 |
| 4,772,269 | 9/1988 | Twardowski et al. ................. | 604/175 |
| 5,090,954 | 2/1992 | Geary ............................. | 604/29 |
| 5,141,499 | 8/1992 | Zappacosta ........................ | 604/175 |
| 5,171,227 | 12/1992 | Twardowstei et al................. | 604/175 |
| 5,192,273 | 3/1993 | Bierman et al. ..................... | 604/174 |
| 5,215,530 | 6/1993 | Hogan ............................. | 604/174 |
| 5,300,032 | 4/1994 | Hibbs et al. ....................... | 604/164.1 |
| 5,314,411 | 5/1994 | Bierman et al. ..................... | 604/174 |
| 5,354,282 | 10/1994 | Bierman ........................... | 604/180 |
| 5,372,589 | 12/1994 | Davis ............................. | 604/180 |
| 5,456,671 | 10/1995 | Bierman ........................... | 604/180 |
| 5,549,645 | 8/1996 | Frey .............................. | 604/29 |
| 5,578,013 | 12/1996 | Bierman ........................... | 604/180 |
| 5,674,201 | 10/1997 | Steinman .......................... | 604/165.03 |
| 5,686,096 | 11/1997 | Khan et al. ....................... | 424/443 |
| 5,702,371 | 12/1997 | Bierman ........................... | 604/180 |
| 5,704,914 | 1/1998 | Stocking et al. .................... | 604/164.07 -- |

UNITED STATES PATENT AND TRADEMARK OFFICE
CERTIFICATE OF CORRECTION

PATENT NO. : 6,358,230 B1
DATED : March 19, 2002
INVENTOR(S) : Davey

It is certified that error appears in the above-identified patent and that said Letters Patent is hereby corrected as shown below:

OTHER DOCUMENTS, add the following Article,
-- Matsumoto M.D., Alan, "PICC Lines: Choosing Devices, Placement and Management," The Second Mid-Atlantic Conference on Angio Access: Establishment and Maintenance of Dialysis and Venous Access, [date unknown], pp. 1-15. --

Signed and Sealed this

Tenth Day of December, 2002

JAMES E. ROGAN
*Director of the United States Patent and Trademark Office*